United States Patent [19]

Avery

[11] 4,071,293

[45] Jan. 31, 1978

[54] CONTACT LENS AND METHOD OF MAKING SAME

[76] Inventor: Theodore P. Avery, 511 W. 6th St., Oil City, Pa. 16301

[21] Appl. No.: 570,943

[22] Filed: Apr. 23, 1975

Related U.S. Application Data

[62] Division of Ser. No. 516,140, Oct. 18, 1974.

[51] Int. Cl.² .............................................. G02B 5/23
[52] U.S. Cl. .................. 351/160; 350/162 R
[58] Field of Search .................................. 351/160–162

[56] References Cited

U.S. PATENT DOCUMENTS

3,431,327  3/1969  Tsuetaki ......................... 351/161 X

FOREIGN PATENT DOCUMENTS

35,302   11/1964   Japan ................................... 351/160
699,736  11/1953   United Kingdom ................. 351/160

*Primary Examiner*—Conrad J. Clark
*Attorney, Agent, or Firm*—Mason, Fenwick & Lawrence

[57] ABSTRACT

A block of plastic is provided with a cylindrical well having an axial pillar in its inner portions over which an annular ferrous ring is mounted. A cylindrical plug is inserted in the well along with a mixture of solvent and powder of the same material as the block, heat and pressure are applied to meld the plug and the block with the ring embedded therein and the block is ground and polished to provide a resultant contact lens that can be removed from the eye of a wearer by a magnet. In another embodiment, the ring can be of various colors for cosmetic effect and can be non-concentric with respect to its axis to provide an offset center of gravity to provide a desired rotational positioning of the lens in the eye of a wearer when the lens is of bifocal or similar type.

7 Claims, 13 Drawing Figures

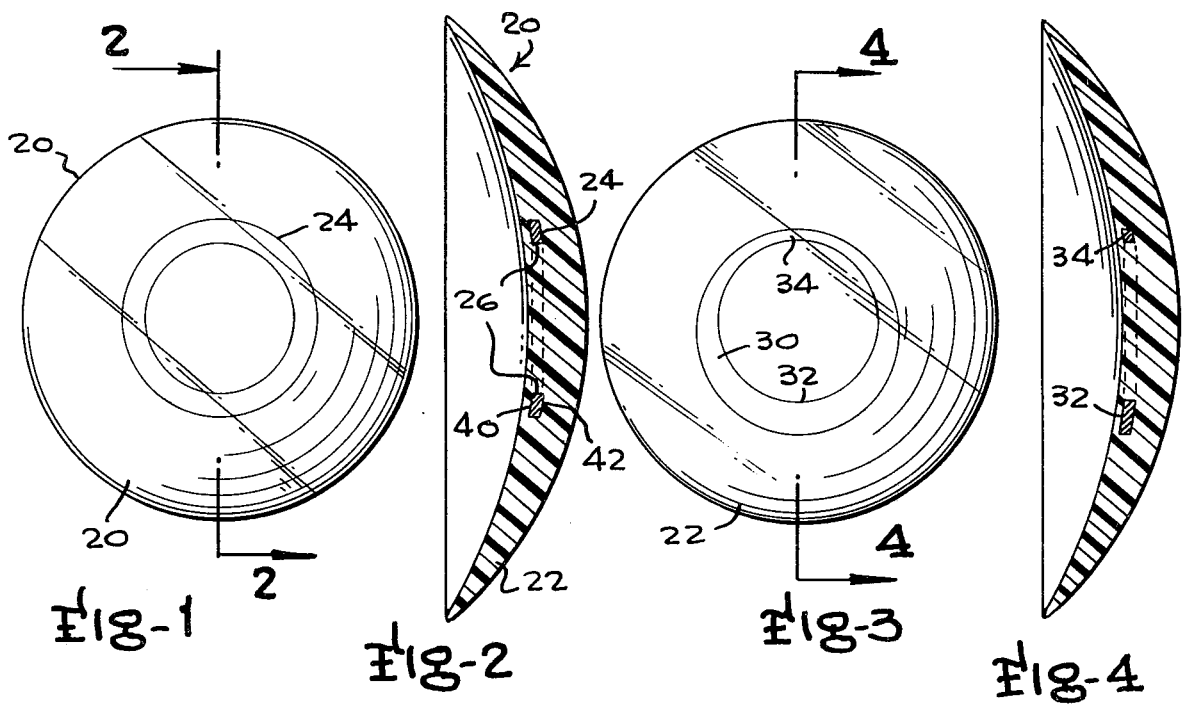
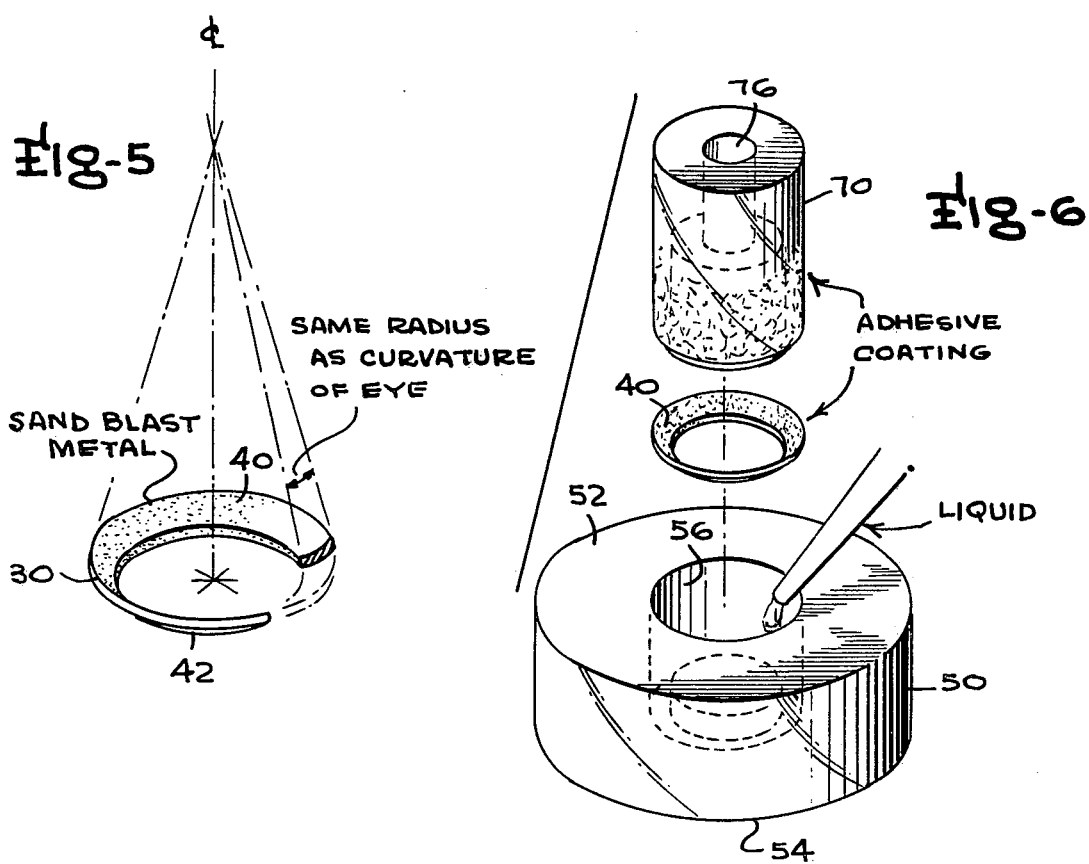

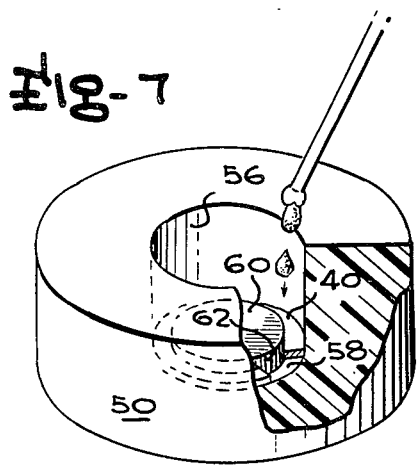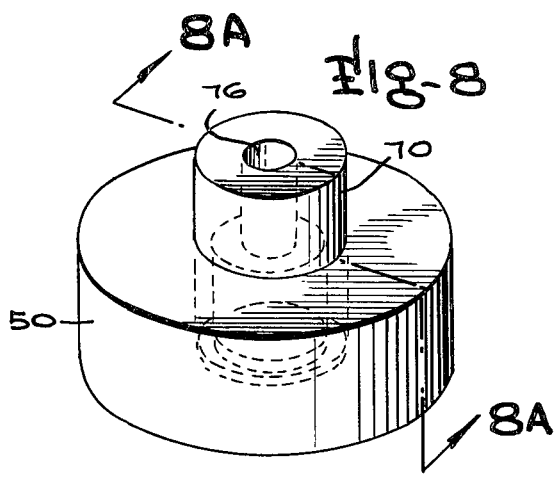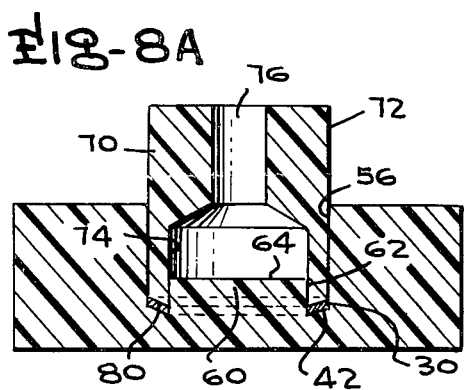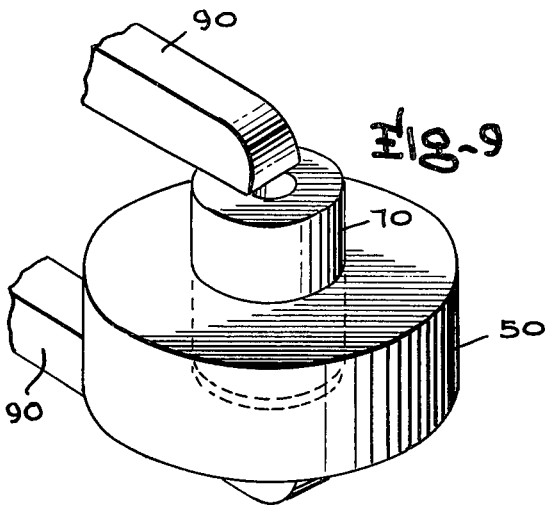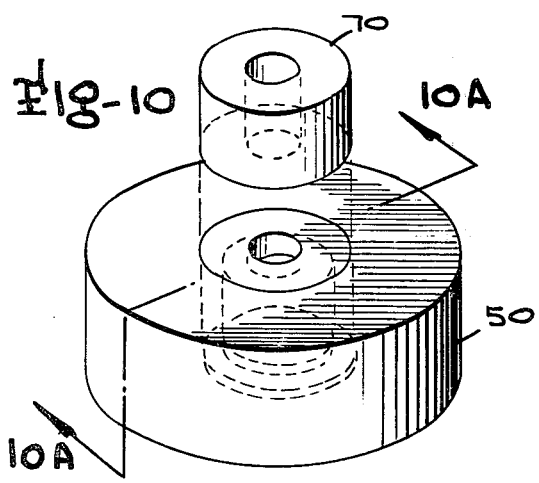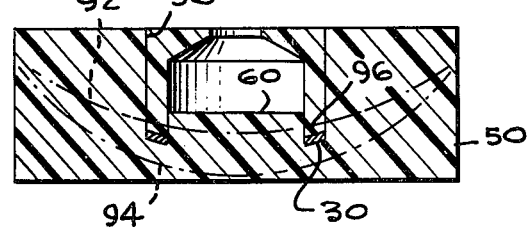

CONTACT LENS AND METHOD OF MAKING SAME

This is a division of application Ser. No. 516,140, filed Oct. 18, 1974.

The subject invention is directed to the field of optics, and is specifically directed to the field of contact lens both of the single focal length and of the bifocal type.

Contact lens have been in use for many years and have achieved a great acceptance notwithstanding several impediments to their usage. One substantial problem encountered with contact lens is the fact that some persons have substantial difficulty in removing the lens from the eye. Moreover, it is extremely easy to drop a contact lens following removal from the eye and consequently subjecting the lens to loss or damage to the substantial personal inconvenience and financial damage to the owner.

Another problem with contact lens arises from the fact that some persons require that the lens be oriented in a given position about its axis to provide the required optical correction for the particular wearer of the lens. A bifocal effect is the most common type of lens requiring proper rotational orientation of the lens and it has been proposed in prior patents such as U.S. Pat. No. 3,431,327 to provide a weight adjacent one edge of the lens for causing the lens to rotate under the influence of gravity to the required position. Unfortunately, a lens of the type disclosed in the aforementioned patent requires that the portion of the lens through which the user's vision extends is formed of two separate bodies of distinct material which can create undesired optical qualities.

Therefore, it is the object of this invention to provide a new and improved method of fabricating a contact lens.

Yet another object of the present invention is the provision of a new and improved contact lens.

A still further object of the invention is the provision of a new and improved contact lens providing enhanced cosmetic effects and which can be easily removed from the eye of a wearer with minimum difficulty and a minimum likelihood of the accidental dropping of the lens.

Achievement of the objects of this invention is enabled through the preferred embodiment for practice of the invention by the provision of a block of lens blank plastic material such as acrylic or the like which has an inwardly extending cylindrical well defined by a cylindrical wall surface. The inner extent of the cylindrical well is defined by an annular surface having a radial component and extending inwardly from the cylindrical surface to a termination with a cylindrical pillar extending outwardly of the well but terminating at an outer end on the interior of the well. An annular ring formed of ferrous material and having an outer diameter slightly less than the diameter of the well is provided for positioning in the well. An inner opening in the annular ring is of a diameter slightly greater than the outer diameter of the cylindrical pillar member and one face of the ring has a curvature approximately the same as the surface of the human eye. This curved surface faces outwardly from the well and faces the eye of the wearer when the contact lens formed from the block is being worn.

The annular ring is preferably formed of ferrous material and is embedded in the block through a process including the provision of a bonding mixture consisting of a solvent and powdered material of the same composition as that of the block. The foregoing mixture is applied to the outer surface of the ring and the inner surface of the well as well as to the outer surface of a cylindrical plug formed of the same material as the block. The cylindrical plug includes an axial opening at one end dimensioned to be matingly received over the pillar member in the bottom of the well and is of the same configuration as the curved face of the ring so as to abuttingly engage the curved face of the ring when inserted in the well. Additionally, the outer diameter of the plug is slightly less than the diameter of the well so that the plug can be inserted in the well to be forcefully urged against the surface of the ring member. Normally, the surface of the ring member is abraded by sand-blasing or the like so that the mixture of solvent and powdered plastic material provides a good and substantial bond to the ring upon the application of heat and pressure which results in a melding of the mixture with the material of the plug and the block to provide a resultant unitary lens blank which is then ground and polished to desired configuration. The portion of the lens through which the user looks is formed completely of the pillar and surrounding portions of the block so that this portion is of uniform composition and optical aberations do not occur as is frequently the case when the optical path passes through lens components formed from different materials.

The annular ring is formed of ferrous material so that a user can remove the ring from the eye by the employment of a hand-held magnet. The annular ring is of progressively continuously varying cross-sectional area so that the thickest cross-sectional area of the ring is diametrically opposite the thinnest cross-sectional area of the ring. Consequently, the center of gravity of the ring does not coincide with the geometric or axial center of the ring. Since the ring member is embedded concentrically within the contact lens, the center of gravity of the contact lens is offset from the geometric center of the lens so that the lens is always rotated by gravity to a fixed position. This fixed position obviously enables a fixed positioning of the optical elements of the lens as required by the particular lens prescription.

Another inventive feature of the foregoing lens construction is that the ring can be formed entirely of material having unique color due to the employment of embedded pigmentation or of a coating of pigmentation so as to provide a lens having a desired cosmetic effect.

A better understanding of the inventive method and structure will be achieved when the following detailed description is considered in conjunction with the appended drawings in which:

FIG. 1 is a front elevation view of a first embodiment of the invention;

FIG. 2 is a sectional view taken along lines 2—2 of FIG. 1;

FIG. 3 is a front elevation view of a second embodiment of the inventive lens;

FIG. 4 is a sectional view taken along lines 4—4 of FIG. 3;

FIG. 5 is a pictorial perspective of the annular ring components with portions removed;

FIG. 6 is an exploded perspective illustrating the components of the inventive method;

FIG. 7 is a perspective of the lens blank block with portions removed illustrating an initial step in the practice of the inventive method;

FIG. 8 is a perspective view of the lens blank block and the plug inserted therein in an intermediate step of the inventive method;

FIG. 8A is a sectional view taken along lines 8A—8A of FIG. 8;

FIG. 9 is a perspective view illustrating a subsequent step in the practice of the inventive method;

FIG. 10 is a perspective view of the lens blank block illustrating a subsequent step in the practice of the inventive method;

FIG. 10A is a sectional view taken along lines 10A—10A of FIG. 10; and

FIG. 11 is a perspective view of a completed lens formed by the inventive method.

Attention is initially invited to FIGS. 1 and 2 of the drawings which illustrate a contact lens, generally designated 20, which is formed of a plastic body portion 22 formed of acrylic or the like and in which an annular ring 24 is mounted. The annular ring 24 can be formed of metal or of composite material including ferrous particles capable of being attracted by a hand-held magnet for removal of the lens from the eye of a user. Additionally, ring 24 can include a surface coating including pigmentation for providing a desired color effect or can be of a solid material embedded with desired pigmentation for cosmetic purposes. It is to be noted that the area of the plastic body member 22 extending within the confines of the inner opening 26 of ring member 24 is the portion of the lens through which light rays travel into a user's eye.

FIGS. 3 and 4 illustrate an embodiment of the invention also including a plastic body portion 22 but differing from the first-discussed embodiment in that an annular ring 30 of non-uniform cross-section is provided embeddedly in the plastic body portion 22. It will be seen that the lower portion 32 of the ring member 30 is substantially larger than the diametrically opposite upper portion 34 of the annular ring 30 so that the heavier portion 32 results in a center of gravity for the ring member 30 below the geometric center of the circular opening 36 of the ring member. Consequently, the center of gravity of the entire lens member is below the geometric center of the lens and the lens always assumes the position illustrated in FIGS. 3 and 4. Consequently, various optical portions of the lens body are always positioned in the same rotational position with respect to the eye of the user. Annular ring 30 of FIGS. 3 and 4 can also be provided with a coating of a desired pigmentation or can be permeated with such pigmentation. Additionally, annular ring 30 can also be of a ferrous metal or include ferrous particles so as to enable attraction of the ring by a magnet to permit an easy removal and retention of the lens from the eye of a user. It is worth noting at this point that the non-uniform shape of the annular ring 30 provides a particularly impressive effect when the ring 30 is of a distinctive color from that of the coloration of the pupil of the eye in which the lens is positioned.

Both embodiments of the lens are produced by essentially the same inventive method which will now be discussed with initial reference being made to FIGS. 5 and 6. FIG. 5 illustrates a non-uniform ring member 30; however, it should be understood that while the inventive method discusses employment of the non-uniform ring member, the method is also equally applicable to the fabrication of a lens employing the uniform ring 24. Therefore, it should be understood that the subsequent discussion of ring 30 would also be applicable to ring 24.

In any event, both of the annular rings include an upper or first face 40 having a curvature approximately the same as the curvature of the human eye. The opposite or second face 42 of the ring member has approximately the same curvature as the first face 40. The primary element of the lens is provided by a lens blank block 50 formed of acrylic methyl methacrylate. Block 50 has an upper surface 52 and a lower surface 54 and includes a cylindrical internal surface 56 defining a well on the interior of the block member. The inner or lower end of the well is defined by an annular end wall 58 shaped and dimensioned to abuttingly engage the lower face 42 of the annular ring members. An axial pillar 60 extends upwardly from the lower end of the well at the inner extent of the annular end wall 58 and has an outer cylindrical surface 62 and a top surface 64. The diameter of outer cylindrical surface 62 is slightly less than the diameter of the opening in the annular ring members which are fitted over the pillars in a mating manner during the lens fabricating process.

The third component employed for the fabrication of a contact lens of the inventive process consists of a cylindrical plug member 70 formed of the same material as block 50 and having an outer cylindrical surface 72 of a diameter slightly less than the diameter of the cylindrical surface 56 defining the downwardly extending well in block member 50. Additionally, plug 70 is provided with an axially extending opening including a lower portion defined by a cylindrical surface 74 of a diameter slightly greater than the diameter of surface 62 of the pillar member 60 so that the surface 74 can be matingly inserted over the surface 62 as best shown in FIG. 8A. The upper portion 76 of the opening in the plug 70 serves as a vent for a purpose to be discussed. The lower end of the plug 70 consists of an annular surface 80 shaped and dimensioned to abuttingly engage the upper face 40 of the annular ring members.

A contact lens is fabricated by the inventive method by initially applying a liquid mixture of solvent and powdered material of the same composition as the block 50 and plug 70 in the interior of the well in the block 50 on surface 58 and adjacent portions of the pillar 60. The plug 70 and the ring 30 are also coated with the mixture of solvent and powder with the mixture comprising four parts liquid monomer and one part acrylic methyl mertacrylate powder in the preferred form for practice of the invention. The plug 70 is also provided with a coating of the mixture as is the annular ring and the annular ring is positioned over the pillar 60 as shown in FIG. 7. Plug 70 is then inserted in the well over the pillar 60 as shown in FIGS. 8 and 8A and pressure is applied by a conventional clamp means 90 to the upper end of the plug 70 and the base surface of the block 50 to extrude gaseous bubbles and excess liquid mixture upwardly in the axial passageway in plug 70 in an obvious manner. The clamp assembly is then heated at approximately 160° F for approximately 5 hours. The assembly is then removed from the heat and the upper extending portion of plug 70 extending above the upper surface of the block 50 is cut off at the top of the block as shown in FIG. 10.

The remaining assembly is then ground and polished to provide an inner eye conforming surface 92 and an outer surface 94 as shown in FIG. 10A having an embedded ring within the confines of the lens member. It will be noted that the optical path of light passing through the lens will travel through portions of the lens formed solely of the block 50 and the pillar portion 60 of the block member. Consequently, the optical path flows through a unitary material to avoid any distortion. The only portions of the plug 70 remaining in the finished lens comprise the annular ring portion 96 immediately to the rear of the ring member as shown in FIG. 10A.

Therefore, it will be obvious that the new and improved method provides a uniquely satisfactory lens construction which has unique qualities enabling positioning and removal of the lens in and from a wearer's eye.

Numerous modifications of the invention will undoubtedly occur to those of skill in the art and it should be understood that the spirit and scope of the invention is to be limited solely by the appended claims.

I claim:

1. A contact lens comprising a plastic lens member having a central axis, a generally annular ring formed of metal susceptible to magnetic attraction and having a continuously varying cross-section embedded in said lens concentrically with respect to the axis of said lens, said ring member being of varying cross-section so that one portion of said ring is thicker than the diametrically opposite portion of said ring so that the center of gravity of said lens and ring assembly is below the geometric center of said lens so that said lens is rotated by gravity to a desired lens orientation in the eye of a person wearing said lens.

2. The invention of claim 1 wherein said ring includes a coating containing pigmentation of a different color from that of the metal so as to provide a desired cosmetic effect for the wearer of said lens.

3. A contact lens comprising a plastic lens member having a central axis, a generally annular ring embedded in said plastic lens member concentrically with respect to the axis of said lens and formed of magnetically attractable material having an outer circular periphery and an inner circular opening having a center of curvature spaced from the center of curvature of said outer circular periphery, said ring member being of varying cross-section so that one portion of said ring is thicker than the diametrically opposite portion of said ring so that the center of gravity of said lens and ring assembly is below the geometric center of said lens so that said lens is rotated by gravity to a desired lens orientation in the eye of a person wearing said lens.

4. The invention of claim 3 wherein said annular ring is formed of material susceptible to magnetic attraction and has an inner face having a curvature approximately the same as the curvature of the human eye.

5. The invention of claim 4 wherein said annular ring has an outer face having approximately the same curvature of said inner face.

6. The invention of claim 5 wherein said annular ring has inner and outer faces each having a curvature approximately the same as the curvature of the human eye.

7. The invention of claim 3 wherein said annular ring has a progressively continuously varying cross-section.

* * * * *